(12) United States Patent
Van Der Heide et al.

(10) Patent No.: US 12,098,125 B2
(45) Date of Patent: Sep. 24, 2024

(54) PROCESS FOR PREPARING DIALKYL CARBONATE AND ALKANEDIOL

(71) Applicant: SHELL OIL COMPANY, Houston, TX (US)

(72) Inventors: Evert Van Der Heide, Amsterdam (NL); Kai Jürgen Fischer, Amsterdam (NL)

(73) Assignee: Shell USA, Inc., Houston, TX (US)

( * ) Notice: Subject to any disclaimer, the term of this patent is extended or adjusted under 35 U.S.C. 154(b) by 275 days.

(21) Appl. No.: 17/642,438

(22) PCT Filed: Sep. 28, 2020

(86) PCT No.: PCT/EP2020/077029
§ 371 (c)(1),
(2) Date: Mar. 11, 2022

(87) PCT Pub. No.: WO2021/063853
PCT Pub. Date: Apr. 8, 2021

(65) Prior Publication Data
US 2022/0340513 A1 Oct. 27, 2022

(30) Foreign Application Priority Data
Oct. 3, 2019 (EP) .................................. 19201292

(51) Int. Cl.
*C07C 68/065* (2020.01)
*C07C 29/48* (2006.01)

(52) U.S. Cl.
CPC ............ *C07C 68/065* (2013.01); *C07C 29/48* (2013.01)

(58) Field of Classification Search
CPC ............................... C07C 68/065; C07C 29/48
See application file for complete search history.

(56) References Cited

U.S. PATENT DOCUMENTS

| | | | |
|---|---|---|---|
| 3,803,201 A | 4/1974 | Gilpin et al. |
| 4,062,884 A | 12/1977 | Romano et al. |
| 4,181,676 A | 1/1980 | Buysch et al. |
| 4,691,041 A | 9/1987 | Duranleau et al. |
| 4,851,555 A | 7/1989 | Weinstein |
| 5,359,118 A | 10/1994 | Wagner et al. |
| 7,763,745 B2 | 7/2010 | Van Der Heide et al. |
| 8,618,322 B2 | 12/2013 | Nisbet et al. |
| 9,096,514 B2 | 8/2015 | Van Der Heide et al. |
| 2011/0313185 A1 | 12/2011 | Shimizu |
| 2012/0101293 A1 | 4/2012 | Ooms et al. |
| 2017/0334816 A1 | 11/2017 | Huizenga et al. |
| 2022/0017450 A1 | 1/2022 | Fishcher et al. |

FOREIGN PATENT DOCUMENTS

| | | | |
|---|---|---|---|
| EP | 0274953 A1 | 7/1988 |
| WO | 2010063694 A1 | 6/2010 |

OTHER PUBLICATIONS

Office Action Received for Chinese Application No. 202080069196. 3, Mailed on Jul. 13, 2023, 19 Pages(10 Pages of English Translation and 9 Pages of Official Copy).
International Search Report and Written Opinion received for PCT Patent Application No. PCT/EP2020/077029, mailed on Dec. 10, 2020, 09 pages.
Knifton et al., "Ethylene Glycol-dimethyl Carbonate Cogeneration", Journal of Molecular Catalysis, vol. 67, 1991, pp. 389-399.
Ullmann, "Ullmann's Encyclopedia of Industrial Chemistry", Reaction cols. 5th Edition, vol. B4, 1992, p. 321ff.
Rogalski et al., "Ebulliometers Modified for the Accurate Determination of Vapour-liquid Equilibrium", Elsevier Scientific Publishing Company, Amsterdam, vol. 5, 1980, pp. 97-112.
International Search Report and Written Opinion received for PCT Patent Application No. PCT/EP2019/085266, mailed on Feb. 18, 2020, 09 pages.
International Search Report and Written Opinion received for PCT Patent Application No. PCT/EP2017/058522, mailed on Jun. 28, 2017, 08 pages.

*Primary Examiner* — Sikarl A Witherspoon
(74) *Attorney, Agent, or Firm* — Shell USA, Inc.

(57) ABSTRACT

The invention relates to a process wherein a dialkyl carbonate stream containing an ether alkanol impurity is subjected to extractive distillation using an extraction solvent to obtain a top stream comprising dialkyl carbonate and a bottom stream comprising the ether alkanol impurity and the extraction solvent, wherein the extraction solvent is an organic compound containing one or more ester moieties and/or ether moieties which organic compound does not contain a hydroxyl group. Further, the invention relates to a process for making a diaryl carbonate, comprising reacting an aryl alcohol with a stream containing a dialkyl carbonate from which stream an ether alkanol impurity has been removed in accordance with the above-described process.

11 Claims, 1 Drawing Sheet

PROCESS FOR PREPARING DIALKYL CARBONATE AND ALKANEDIOL

CROSS REFERENCE TO RELATED APPLICATIONS

This is a National stage application of International application No PCT/EP2020/077029, filed Sep. 28, 2020, which claims priority of European application No. 19201292.0, filed Oct. 3, 2019 which is incorporated herein by reference in its entirety.

FIELD OF THE INVENTION

The present invention relates to a process for the preparation of a dialkyl carbonate and an alkanediol from an alkylene carbonate and an alkanol.

BACKGROUND OF THE INVENTION

Dialkyl carbonates can be produced by reaction of alkylene carbonate with alkanol. Where alkylene carbonate (such as ethylene carbonate) is reacted with alkanol (such as ethanol), the products are dialkyl carbonate (such as diethyl carbonate) and alkanediol (such as monoethylene glycol). Such process is well known and an example thereof is disclosed in U.S. Pat. No. 5,359,118. This document discloses a process in which di($C_1$-$C_4$ alkyl) carbonates and alkanediols are prepared by transesterification of an alkylene carbonate with a $C_1$-$C_4$ alkanol.

At various points within said total process for producing dialkyl carbonate from alkylene carbonate, one or more ether alkanol (i.e. alkoxy alkanol) impurities may be produced. For example, in a reactor where ethanol and ethylene carbonate are reacted into diethyl carbonate and monoethylene glycol, a side-reaction of ethanol with ethylene oxide, formed by back-reaction of ethylene carbonate into ethylene oxide and carbon dioxide, into 2-ethoxyethanol (ethyl oxitol or ethylene glycol monoethyl ether) may take place. Further, ethyl oxitol may be formed by a side-reaction of ethanol with ethylene carbonate in such a way that carbon dioxide is released and ethyl oxitol is produced. Still further, a side-reaction between ethanol and monoethylene glycol may take place producing ethyl oxitol and water. Still even further, ethyl oxitol may be formed via decarboxylation of hydroxyethyl ethyl carbonate.

Therefore, the product stream from a reactor where ethanol and ethylene carbonate are reacted into diethyl carbonate and monoethylene glycol, may comprise unconverted ethanol, unconverted ethylene carbonate, diethyl carbonate, monoethylene glycol and the above-mentioned ethyl oxitol impurity. The presence of said alkoxy alkanol impurity may be detrimental in any subsequent production process. Said alkoxy alkanol impurity may for example end up in the dialkyl carbonate that is used as a starting material for the synthesis of diphenyl carbonate from said dialkyl carbonate and phenol. For example, in a case where the dialkyl carbonate is diethyl carbonate and the alkoxy alkanol impurity is ethyl oxitol, said ethyl oxitol may react with the phenol starting material and/or with the diphenyl carbonate product.

Direct reaction of phenol and ethyl oxitol may result in the production of phenyl 2-ethoxyethyl ether, and hence in the loss of valuable phenol reactant. Further, such reaction results in the introduction of undesired chemicals in the process and therefore to separation issues.

Reaction of diphenyl carbonate with ethyl oxitol results in product loss as phenyl 2-ethoxyethyl carbonate is produced. Further, the latter product acts as a "poison" in any subsequent polymerisation of diphenyl carbonate into polycarbonate material. For example, when diphenyl carbonate is reacted with bis-phenol A (BPA), polycarbonate and phenol are formed. Diphenyl carbonate can react with BPA since phenol is a relatively good leaving group. Dialkyl carbonates (such as diethyl carbonate) however cannot be used to produce polycarbonate by reaction with BPA, since alkanols are not good leaving groups. Alkoxy alkanols (such as ethyl oxitol) are neither good leaving groups. Therefore, in case phenyl 2-ethoxyethyl carbonate is present in a diphenyl carbonate feed to be reacted with BPA, phenol will be released easily from said phenyl 2-ethoxyethyl carbonate but not ethyl oxitol which will consequently stop the polymerization process at one end of the chain. Consequently, phenyl 2-ethoxyethyl carbonate has to be removed from diphenyl carbonate before the latter is contacted with BPA.

The above exemplifies that in a case where a dialkyl carbonate stream containing an ether alkanol impurity is formed, it is desired to remove said ether alkanol impurity before any subsequent process takes place wherein the dialkyl carbonate is transformed into a valuable end product. For example, it is needed to remove any ethyl oxitol impurity from a diethyl carbonate stream containing said impurity before reaction of the diethyl carbonate with phenol takes place.

Referring to the above example where ethanol and ethylene carbonate have been reacted into diethyl carbonate and monoethylene glycol, the product stream also containing unconverted ethanol and ethylene carbonate and ethyl oxitol side-product, may be separated by means of distillation. The boiling points for the various components in said product stream are mentioned in the table below.

|  | Boiling point (° C.) |
|---|---|
| ethanol | 78.4 |
| diethyl carbonate | 126-128 |
| ethyl oxitol | 135 |
| monoethylene glycol | 197.3 |
| ethylene carbonate | 260.4 |

The distillation as referred to above may result in a top stream containing diethyl carbonate and unconverted ethanol and a bottom stream containing monoethylene glycol and unconverted ethylene carbonate. Most likely, all of the ethyl oxitol ends up in the top stream. However, depending on the specific conditions under which distillation is carried out, part of the ethyl oxitol may end up in the bottom stream. Subsequently, said top stream may be further separated by means of distillation into a top stream containing unconverted ethanol which can be recycled to the reactor where diethyl carbonate and monoethylene glycol are produced, and a bottom stream containing diethyl carbonate and the ethyl oxitol impurity.

As discussed above, before a dialkyl carbonate is transformed into a valuable end product in any subsequent process, the ether alkanol impurity has to be removed therefrom as that might interfere said subsequent process and/or any further processes. For the above example, this means that the ethyl oxitol impurity should be removed from the bottom stream containing diethyl carbonate and the ethyl oxitol impurity. In principle, ethyl oxitol and diethyl carbonate could be separated by means of a further distillation step. However, because of the small difference in boiling point between diethyl carbonate and ethyl oxitol (see above table), such separation is very cumbersome requiring many distillation steps and stages.

Similarly, in a case wherein ethanol and propylene carbonate have been reacted into diethyl carbonate and monopropylene glycol, ethyl proxitol may be formed as an ether alkanol impurity. Ethyl proxitol (propylene glycol monoethyl ether) comprises 1-ethoxy-2-propanol and/or 2-ethoxy-1-propanol. In this case there is also a small difference in boiling point between diethyl carbonate (126-128° C.) and the ether alkanol impurity (1-ethoxy-2-propanol: 132° C.; 2-ethoxy-1-propanol: 138° C.), making separation by distillation very cumbersome.

Therefore, there is a need to remove an ether alkanol impurity from a dialkyl carbonate stream containing such ether alkanol impurity. WO2010046320 discloses a process for removing an ether alkanol impurity from a stream containing an organic carbonate (e.g. a dialkyl carbonate) and the ether alkanol impurity, comprising contacting the stream with a catalyst to effect reaction of the ether alkanol impurity with the organic carbonate. In specific, WO2010046320 discloses a process for the preparation of a dialkyl carbonate and an alkanediol, wherein in one of the process steps a stream containing dialkyl carbonate and the ether alkanol impurity is contacted with a catalyst to effect reaction of the ether alkanol impurity with the dialkyl carbonate.

A disadvantage of the ether alkanol impurity removal process as disclosed in above-mentioned WO2010046320 is that a catalyst needs to be introduced to react away the impurity. There are several disadvantages associated with using a catalyst. For example, after some time a catalyst may become deactivated and then needs to be replaced. Further, it may be possible that impurities leach from the catalyst thereby contaminating process streams and the desired product, which may result in the need for bleed and/or further purification.

In addition to using a catalyst which may be cumbersome, another disadvantage of the process as disclosed in said WO2010046320 is that valuable dialkyl carbonate gets lost since the ether alkanol impurity reacts with a dialkyl carbonate. In such reaction, a carbonate derived from 2 ether alkanol molecules (e.g. ethyl oxitol) is formed, thereby not only loosing diethyl carbonate but also the ether alkanol. Yet another disadvantage is that an additional step is needed, namely a distillation to separate said heavy carbonate derived from 2 ether alkanols from the desired dialkyl carbonate.

As mentioned above, in the process as disclosed in WO2010046320, not only valuable dialkyl carbonate gets lost but also the ether alkanol which as such is also a valuable chemical. For example, ether alkanols (e.g. ethyl oxitol) may be used as a solvent in paints.

Therefore, it is an object of the present invention to provide a simple, effective and efficient method of removing an ether alkanol impurity from a dialkyl carbonate stream containing such impurity, which stream may be formed in a process for the preparation of a dialkyl carbonate and an alkanediol, which removal method preferably does not have one or more of the above-mentioned disadvantages.

SUMMARY OF THE INVENTION

Surprisingly it was found that the above object may be achieved by a process wherein a dialkyl carbonate stream containing the ether alkanol impurity is subjected to extractive distillation using an extraction solvent to obtain a top stream comprising dialkyl carbonate and a bottom stream comprising the ether alkanol impurity and the extraction solvent, wherein the extraction solvent is an organic compound containing one or more ester moieties and/or ether moieties which organic compound does not contain a hydroxyl group.

Accordingly, the present invention relates to a process for the preparation of a dialkyl carbonate and an alkanediol, comprising:

(a) reacting an alkylene carbonate and an alkanol to obtain a product mixture containing unconverted alkylene carbonate, unconverted alkanol, dialkyl carbonate, alkanediol and an ether alkanol impurity;

(b) separating unconverted alkylene carbonate and alkanediol from the product mixture to obtain a top stream containing unconverted alkanol, dialkyl carbonate and the ether alkanol impurity;

(c) recovering the alkanediol;

(d) separating unconverted alkanol from the top stream obtained in step (b) to obtain a bottom stream containing dialkyl carbonate and the ether alkanol impurity; and (e) subjecting the bottom stream obtained in step (d) to extractive distillation using an extraction solvent to obtain a top stream comprising dialkyl carbonate and a bottom stream comprising the ether alkanol impurity and the extraction solvent, wherein the extraction solvent is an organic compound containing one or more ester moieties and/or ether moieties which organic compound does not contain a hydroxyl group; and (f) removing the ether alkanol impurity from the bottom stream obtained in step (e) and recycling the extraction solvent to step (e).

The present invention also relates to a process for removing an ether alkanol impurity from a stream containing a dialkyl carbonate and the ether alkanol impurity, comprising the above-mentioned steps (e) and (f).

Further, the present invention relates to a process for making a diaryl carbonate, comprising reacting an aryl alcohol with a stream containing a dialkyl carbonate from which stream an ether alkanol impurity has been removed in accordance with the above-described process.

DETAILED DESCRIPTION OF THE INVENTION

The process of the present invention comprises steps (a) to (f), as described hereinbelow. Said process may comprise one or more intermediate steps between steps (a) and (b), between steps (b) and (c), between steps (c) and (d), between steps (d) and (e), and between steps (e) and (f). Further, said process may comprise one or more additional steps preceding step (a) and/or following step (f).

While the process of the present invention and mixtures or streams or catalysts used or produced in said process are described in terms of "comprising", "containing" or "including" one or more various described steps and components, respectively, they can also "consist essentially of" or "consist of" said one or more various described steps and components, respectively.

In the context of the present invention, in a case where a mixture or a stream or a catalyst comprises two or more components, these components are to be selected in an overall amount not to exceed 100%.

Further, where upper and lower limits are quoted for a property then a range of values defined by a combination of any of the upper limits with any of the lower limits is also implied.

Unless indicated otherwise, where in the present specification reference is made to a boiling point this means the boiling point at 760 mm Hg pressure.

In the present invention, an ether alkanol impurity is removed from a stream containing a dialkyl carbonate and the ether alkanol impurity. An ether alkanol is identical to an alkoxy alkanol, and both terms are used interchangeably in the present specification.

The process of the present invention is characterized by the following steps (e) and (f) involving extractive distillation:

(e) subjecting a stream containing a dialkyl carbonate and an ether alkanol impurity to extractive distillation using an extraction solvent to obtain a top stream comprising dialkyl carbonate and a bottom stream comprising the ether alkanol impurity and the extraction solvent, wherein the extraction solvent is a specific extraction solvent as further described hereinbelow; and (f) removing the ether alkanol impurity from the bottom stream obtained in step (e) and recycling the extraction solvent to step (e).

Surprisingly, it has appeared that the presence of the above-mentioned solvent used in step (e) of the present process in a distillation column changes the relative volatility of a dialkyl carbonate versus an alkanol ether impurity and advantageously breaks the azeotrope that exists between the two. Further, the dialkyl carbonate is separated via the top stream from such column and the alkanol ether impurity is separated via the bottom stream together with said solvent. Thus, advantageously, said solvent is a good extraction solvent for separating an alkanol ether impurity from a dialkyl carbonate in an extractive distillation process, i.e. in accordance with step (e) of the present process. Surprisingly, said solvent preferably dissolves the alkanol ether impurity and to a lesser extent the dialkyl carbonate. In a further step, the alkanol ether impurity is easily separated from the extraction solvent, for example by distillation, after which the extraction solvent can advantageously be re-used in extractive distillation of mixtures of dialkyl carbonate and alkanol ether impurity.

In EP2380868A1, extractive distillation in a process for producing diethyl carbonate from ethylene or propylene carbonate and ethanol is also disclosed. Claims 11 to 14 of said EP2380868A1 concern a process for producing diethyl carbonate, comprising performing a transesterification reaction of ethylene carbonate or propylene carbonate with ethanol, wherein the process comprises a step of subjecting the reaction product obtained in said transesterification reaction to extractive distillation using ethylene glycol or propylene glycol as the extraction solvent to separate by distillation a fraction containing an ether compound. Such ether compound may be the above-mentioned ethyl oxitol or ethyl proxitol.

Figure 1:
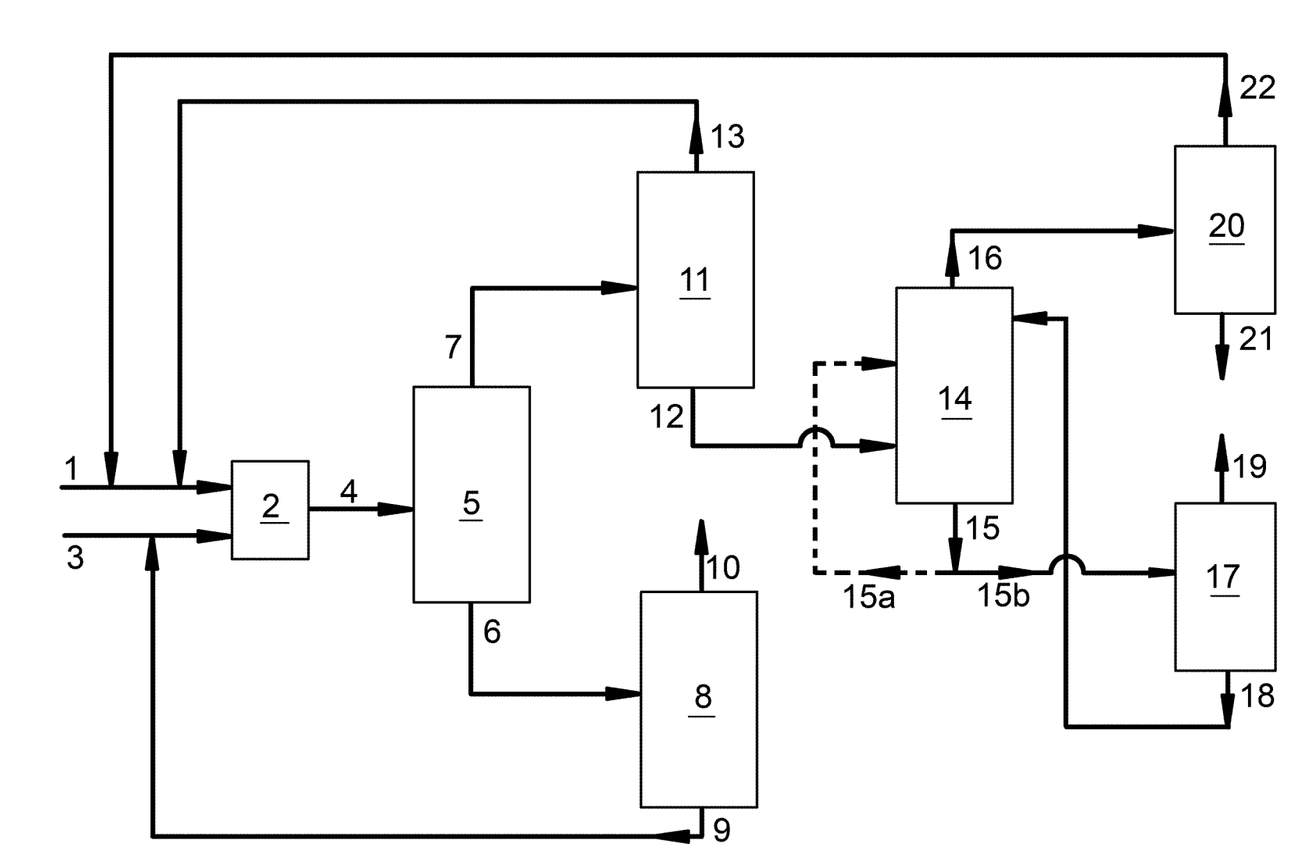
FIG. 1 is a schematic diagram showing a process for the preparation of a dialkyl carbonate and an alkanediol from an alkylene carbonate and an alkanol in accordance with the present invention wherein an ether alkanol impurity is removed from a stream containing dialkyl carbonate and the ether alkanol impurity.

According to claim 12 of said EP2380868A1, the above-mentioned extractive distillation is performed in a step II of separating by distillation the reaction product into a low-boiling fraction mainly comprising ethanol and diethyl carbonate and a high-boiling fraction mainly comprising ethylene carbonate or propylene carbonate and ethylene glycol or propylene glycol. Reference is also made to FIG. 1, paragraph [0066] and Examples 1-3 of said EP2380868A1. A disadvantage of subjecting such (raw) reaction product stream to extractive distillation is that the volume of such stream is relatively large. Such large volume reaction product stream in combination with the extraction solvent requires a relatively large distillation column, which is cumbersome. Advantageously, the further purified bottom stream containing dialkyl carbonate and the ether alkanol impurity obtained in step (d) of the present process has a relatively low volume, so that a relatively small distillation column may be used.

Further, a disadvantage of using either ethylene glycol or propylene glycol as the extraction solvent as disclosed in said EP2380868A1, is that said ethylene glycol or propylene glycol may be converted back in situ during extractive distillation to the corresponding cyclic carbonate by reaction with dialkyl carbonate (e.g. diethyl carbonate), especially at a relatively high distillation temperature and/or in the presence of a (homogenous) catalyst which would still be present in said (raw) reaction product stream. This is undesired, as this results in a loss of extraction solvent and a loss of valuable dialkyl carbonate product. In the present process, such conversion of the extraction solvent is advantageously avoided as the extraction solvent used in the present invention substantially does not react with dialkyl carbonate, especially since no catalyst is present in the above-mentioned further purified bottom stream obtained in step (d) of the present process.

Still further, in the process of said EP2380868A1, the ether impurity has to be separated from the ethylene or propylene glycol extraction solvent, to a relatively great extent to meet the quality standard for said ethylene or propylene glycol which is not only used as an extraction solvent but which is also one of the desired products. Finally, after such cumbersome sharp separation, the ether compound ends up in a (waste) water stream. In case one wishes to recover the ether compound and/or to make said water stream suitable for disposal, one would have to perform yet another separation to separate the ether compound from the water. Such additional purification step is also cumbersome and undesired.

In the present invention, the extraction solvent to be used in step (e) is an organic compound containing one or more ester moieties and/or ether moieties, preferably one or more ester moieties, which organic compound does not contain a hydroxyl group. An ester moiety is of formula —(C=O)O—. A specific example of such ester moiety is a carbonate moiety which is of formula —O(C=O)O—. An ether moiety is of formula —O—. A carbonate moiety is considered to comprise 2 ester moieties. More preferably, said organic compound contains two ester moieties, most preferably one carbonate moiety. As mentioned above, said organic compound does not contain a hydroxyl group. It is preferred that said organic compound consists of carbon atoms and hydrogen atoms, with the proviso that in addition said organic compound contains one or more oxygen atoms as present in said ester moieties and/or ether moieties.

The extraction solvent to be used in step (e) may be an ester of formula $R_1X(C=O)OR_2$ wherein X is absent or is an oxygen atom and wherein $R_1$ and $R_2$ comprise a total of 2 to 20 carbon atoms and do not contain a hydroxyl group. This means that the total number of carbon atoms for $R_1$ and $R_2$ together is 2 to 20. Preferably, X is an oxygen atom, in which case the ester is a carbonate. $R_1$ and $R_2$ comprise a total of 2 to 20 carbon atoms, suitably 3 to 15 carbon atoms, more suitably 3 to 10 carbon atoms, most suitably 3 to 5 carbon atoms. $R_1$ and $R_2$ may be an alkyl group or an aryl group, preferably an alkyl group. In addition, in the case where X is absent, $R_1$ may be $R_3O(O=C)$— and $R_3$ may be an alkyl group or an aryl group, preferably an alkyl group. Further, $R_1$ and $R_2$ may be connected to form a ring, which ring may consist of 5 to 7 atoms, preferably 5 or 6 atoms, more preferably 5 atoms, which ring may be substituted by one or more alkyl or aryl groups. Further, $R_1$ and $R_2$ may contain one or more ester and/or ether moieties.

One suitable class of esters of the above-mentioned formula $R_1X(C=O)OR_2$, wherein $R_1$ and $R_2$ do not contain a hydroxyl group, are esters wherein X is absent and which originate from reacting an alkanol of formula $R_2OH$ containing 1 or more hydroxyl groups with a carboxylic acid of formula $R_2(C=O)OH$, wherein all of the 1 or more hydroxyl groups of the alkanol are esterified. Said alkanol contains 1 or more hydroxyl groups, suitably 2 or more hydroxyl groups, more suitably 3 or more hydroxyl groups, more suitably 3 to 5 hydroxyl groups, more suitably 3 or 4 hydroxyl groups, most suitably 3 hydroxyl groups. Further, said alkanol may contain 3 to 10 carbon atoms, suitably 3 to 8 carbon atoms, more suitably 3 to 6 carbon atoms, most suitably 3 to 4 carbon atoms. Preferably, said alkanol contains at least 2, more preferably at least 3, carbon atoms and at least 2, more preferably at least 3, hydroxyl groups, in which alkanol each hydroxyl group is bonded to a different carbon atom. Suitable examples of said alkanol are ethylene glycol, propylene glycol, 1,2-butanediol, 1,2-hexanediol, glycerol, erythritol, xylitol and sorbitol, more suitably glycerol, erythritol and xylitol, even more suitably glycerol and erythritol, most suitably glycerol. Said carboxylic acid may contain one or more carboxyl groups, suitably 1 to 4 carboxyl groups, more suitably 1 or 2 carboxyl groups, most suitably 1 carboxyl group. A carboxyl group is of formula —C(=O)OH. Further, said carboxylic acid may contain 1 to 10 carbon atoms, suitably 1 to 8 carbon atoms, more suitably 1 to 6 carbon atoms, most suitably 1 to 4 carbon atoms. Suitable examples of monocarboxylic acids are formic acid, acetic acid and propionic acid, more suitably formic acid and acetic acid. Suitable examples of dicarboxylic acids are oxalic acid, malonic acid, succinic acid and adipic acid, more suitably oxalic acid, malonic acid and succinic acid, most suitably oxalic acid and malonic acid. Specific examples of the esters described in this paragraph are: glycerol triformate, glycerol triacetate, ethylene glycol oxalate, ethylene glycol malonate, propylene glycol oxalate, propylene glycol malonate, 1,2-butanediol oxalate, 1,2-butanediol malonate, 1,2-hexanediol oxalate and 1,2-hexanediol malonate.

Another suitable, preferred class of esters of the above-mentioned formula $R_1X(C=O)OR_2$, wherein $R_1$ and $R_2$ do not contain a hydroxyl group, are alkylene carbonates wherein X is an oxygen atom and $R_1$ and $R_2$ are connected to form a ring. The total number of carbon atoms, excluding the one or more carbon atoms present in the one or more carbonate moieties, of the alkylene carbonate is at least 2 and may be of from 2 to 15, more suitably of from 2 to 10, most suitably of from 2 to 5. The ring of the alkylene carbonate may consist of 5 to 7 atoms, preferably 5 or 6 atoms, more preferably 5 atoms, which ring may be substituted by one or more alkyl or aryl groups. The alkylene carbonate may originate from reacting an alkanol containing 2 or more hydroxyl groups with carbon dioxide, wherein all of the 2 or more hydroxyl groups of the alkanol are esterified. The alkanol may be an alkanol as described above for the alkanol of formula $R_2OH$, with the proviso that the alkanol contains an even number of hydroxyl groups. Thus, the alkylene carbonate may for example be an alkylene carbonate of ethylene glycol, propylene glycol, 1,2-butanediol, 1,2-hexanediol, erythritol or sorbitol, more suitably ethylene glycol, propylene glycol or erythritol, even more suitably ethylene glycol or propylene glycol, most suitably ethylene glycol. Preferably, the alkylene carbonate is ethylene carbonate, propylene carbonate, 1,2-butanediol carbonate or 1,2-hexanediol carbonate, more preferably ethylene carbonate or propylene carbonate, most preferably ethylene carbonate. The way in which the alkylene carbonate has been prepared is not essential in the process of the present invention. For example, alternatively, the alkylene carbonate may originate from reacting an alkylene oxide with carbon dioxide. Suitable examples of said alkylene oxide are ethylene oxide and propylene oxide.

It is preferred that the above-mentioned alkylene carbonate that may be used as extraction solvent in step (e) is identical to the alkylene carbonate used as reactant in step (a). An advantage is that by using the same alkylene carbonate no chemical is introduced as extraction solvent, which is new to the overall process for the preparation of a dialkyl carbonate and an alkanediol from an alkylene carbonate and an alkanol.

Yet another suitable class of esters of the above-mentioned formula $R_1X(C=O)OR_2$, wherein $R_1$ and $R_2$ do not contain a hydroxyl group, are carbonates wherein X is an oxygen atom and $R_1$ and $R_2$ are not connected to form a ring. For said non-cyclic carbonates, $R_1$ and $R_2$ may each comprise at least 3 carbon atoms. Suitably, each of $R_1$ and $R_2$ comprises of from 3 to 15, more suitably of from 3 to 10, most suitably of from 3 to 5 carbon atoms.

Further, the extraction solvent to be used in step (e) may be an ether of formula $R_4$—O—$R_5$ wherein $R_4$ and $R_5$ comprise a total of 2 to 20 carbon atoms and do not contain a hydroxyl group. This means that the total number of carbon atoms for $R_4$ and $R_5$ together is 2 to 20. $R_4$ and $R_5$ comprise a total of 2 to 20 carbon atoms, suitably 3 to 15 carbon atoms, more suitably 3 to 10 carbon atoms, most suitably 3 to 6 carbon atoms. $R_4$ and $R_5$ may be an alkyl group or an aryl group, preferably an alkyl group. Further, $R_4$ and $R_5$ may contain one or more ester and/or ether moieties.

One suitable class of ethers of the above-mentioned formula $R_4$—O—$R_5$ are ethers of polyalkylene glycols wherein the polyalkylene glycol may contain 2 to 4 carbon atoms, suitably 2 or 3 carbon atoms, more suitably 2 carbon atoms, and contains two hydroxyl groups which are both etherified with an alkanol which may contain 1 to 4 carbon atoms, more preferably 1 or 2 carbon atoms, most preferably 1 carbon atom. Suitable examples of the latter alkanol are methanol, propanol and butanol, most suitably methanol. Specific examples of the polyalkylene glycols described in this paragraph are: diethylene glycol, triethylene glycol and dipropylene glycol. Further, a specific example of the polyalkylene glycol ether described in this paragraph is the dimethyl ether of diethylene glycol (diglyme).

Another suitable class of ethers of the above-mentioned formula $R_4$—O—$R_5$ are ethers of an alkanol of formula $R_4OH$ containing 1 or more, preferably 2 or more, hydroxyl groups, and an alkanol of formula $R_5OH$ containing 1 or more hydroxyl groups, wherein all of the hydroxyl groups of said alkanols are etherified. The alkanol of formula $R_4OH$ containing 1 or more hydroxyl groups may be an alkanol as described above for the alkanol of formula $R_2OH$. Thus, the ether may for example be an alkyl ether of ethylene glycol, propylene glycol, 1,2-butanediol, 1,2-hexanediol, glycerol, erythritol, xylitol or sorbitol, more suitably glycerol, erythritol or xylitol, even more suitably glycerol or erythritol, most suitably glycerol. For example, the ether may be a trialkyl glycerol ether, wherein the alkyl group may be any alkyl group, including for example methyl and ethyl.

Yet another suitable class of ethers of the above-mentioned formula $R_4$—O—$R_5$ are acetals and ketals. Acetals are obtained by reaction of an alkanol with an aldehyde (for example acetaldehyde), whereas ketals are obtained by reaction of an alkanol with a ketone (for example acetone). The acetals and ketals may be of formula $(R_6)(R_7)C(OR_8)_2$, wherein each of $R_7$ and $R_8$ is an alkyl or aryl group, preferably an alkyl group, and $R_6$ is either (i) a hydrogen atom (acetal) or (ii) an alkyl or aryl group, preferably an alkyl group (ketal). $R_6$, $R_7$ and $R_8$ do not contain a hydroxyl group. In said acetals and ketals, the two $R_8$ groups may be connected to form a ring, which ring may consist of 5 to 7 atoms, preferably 5 or 6 atoms, more preferably 5 atoms. Said ring may be substituted by one or more alkyl or aryl groups. Said cyclic acetal or ketal may originate from reacting an alkanol containing 2 or more hydroxyl groups with either an aldehyde or a ketone, wherein all of the 2 or more hydroxyl groups of the alkanol are etherified. The alkanol may be an alkanol as described above for the alkanol of formula $R_2OH$, with the proviso that the alkanol preferably contains an even number of hydroxyl groups. Thus, the cyclic acetal or ketal may for example be a cyclic acetal or ketal of ethylene glycol, propylene glycol, 1,2-butanediol, 1,2-hexanediol, erythritol or sorbitol, more suitably ethylene glycol, propylene glycol or erythritol, even more suitably ethylene glycol or propylene glycol, most suitably ethylene glycol.

Further, it is envisaged that the extraction solvent to be used in step (e) may be both an ester as defined above and an ether as defined above.

Further, in the present invention, the extraction solvent to be used in step (e) either has no boiling point (i.e. thermal decomposition at high temperature) or has a boiling point which is preferably higher than the boiling point of the dialkyl carbonate. If the extraction solvent has a boiling point, this is preferably at least 10° C. higher, more preferably at least 30° C. higher, most preferably at least 50° C. higher than the boiling point of the dialkyl carbonate.

Step (a) of the present process for the preparation of a dialkyl carbonate and an alkanediol comprises reacting an alkylene carbonate and an alkanol to obtain a product mixture containing unconverted alkylene carbonate, unconverted alkanol, dialkyl carbonate, alkanediol and an ether alkanol impurity.

Thus, step (a) of the process of the present invention includes the reaction of an alkylene carbonate with an alkanol. Said alkylene carbonate may be a $C_2$-$C_6$ alkylene carbonate, more suitably a $C_2$-$C_4$ alkylene carbonate, most suitably a $C_2$-$C_3$ alkylene carbonate. Preferably, said alkylene carbonate is ethylene carbonate or propylene carbonate, most preferably ethylene carbonate. The nature of the alkylene carbonate determines the nature of the alkanediol product: for example, reaction of ethylene carbonate with an alkanol results in monoethylene glycol, which is 1,2-ethanediol (the alkanediol).

Further, said alkanol may be a $C_1$-$C_4$ alkanol, more suitably a $C_1$-$C_3$ alkanol, most suitably a $C_2$-$C_3$ alkanol. Preferably, said alkanol contains 1 or 2 hydroxy groups, most preferably 1 hydroxy group. Further, preferably, said alkanol is methanol, ethanol or isopropanol, more preferably ethanol or isopropanol, most preferably ethanol. The nature of the alkanol determines the nature of the dialkyl carbonate product: for example, reaction of an alkylene carbonate with ethanol results in diethyl carbonate (the dialkyl carbonate).

The product mixture obtained in step (a) contains an ether alkanol impurity. As mentioned above, an ether alkanol is identical to an alkoxy alkanol. An alkoxy alkanol is an alkanol of formula $R_3OH$ wherein $R_3$ is an alkoxyalkyl group. The alkoxy part in said alkoxyalkyl group is directly or indirectly derived from the alkanol used in step (a), whereas the alkyl part in said alkoxyalkyl group is directly or indirectly derived from the alkylene carbonate used in step (a). Therefore, the same preferences apply as discussed above with reference to the alkanol and alkylene carbonate used in step (a). For example, the alkoxy part in said alkoxyalkyl group is preferably methoxy, ethoxy or isopropoxy, more preferably ethoxy or isopropoxy, most preferably ethoxy. Further, for example, the alkyl part in said alkoxyalkyl group is preferably ethyl or propyl, most preferably ethyl. The ether alkanol impurity may for example be 2-ethoxyethanol or 1-ethoxy-2-propanol and/or 2-ethoxy-1-propanol.

In a particularly preferred embodiment, the alkylene carbonate is ethylene carbonate, the alkanol is ethanol, the dialkyl carbonate is diethyl carbonate, the alkanediol is monoethylene glycol and the ether alkanol impurity is 2-ethoxyethanol. 2-Ethoxyethanol may also be referred to as ethyl oxitol.

In another particularly preferred embodiment, the alkylene carbonate is propylene carbonate, the alkanol is ethanol, the dialkyl carbonate is diethyl carbonate, the alkanediol is monopropylene glycol and the ether alkanol impurity is ethyl proxitol (propylene glycol monoethyl ether) which comprises 1-ethoxy-2-propanol and/or 2-ethoxy-1-propanol.

Preferably, in step (a) of the process of the present invention a catalyst is used, more specificly a transesterification catalyst.

The transesterification catalyst that may be used in step (a) of the present process may be one of many suitable homogeneous and heterogeneous transesterification catalysts known from prior art.

For example, suitable homogeneous transesterification catalysts have been described in U.S. Pat. No. 5,359,118 and include hydrides, oxides, hydroxides, alkanolates, amides, or salts of alkali metals, i.e., lithium, sodium, potassium, rubidium and cesium. Preferred homogeneous transesterification catalysts are hydroxides or alkanolates of potassium or sodium. Other suitable homogeneous transesterification catalysts are alkali metal salts, such as acetates, propionates, butyrates, or carbonates. Suitable catalysts are described in U.S. Pat. No. 5,359,118 and the references mentioned therein, such as EP274953A, U.S. Pat. No. 3,803,201, EP1082A, and EP180387A.

As mentioned above, it is also possible to employ a heterogeneous transesterification catalyst. In the present process, the use of a heterogeneous transesterification catalyst in step (a) is preferred. Suitable heterogeneous catalysts include ion exchange resins that contain functional groups. Suitable functional groups include tertiary amine groups and quaternary ammonium groups, and also sulphonic acid and carboxylic acid groups. Further suitable catalysts include alkali metal and alkaline earth metal silicates. Suitable catalysts have been disclosed in U.S. Pat. Nos. 4,062,884 and 4,691,041. The heterogeneous catalyst may be selected from ion exchange resins comprising a polystyrene matrix and tertiary amine functional groups. An example is Amberlyst A-21 (ex Rohm & Haas) comprising a polystyrene matrix to which N,N-dimethylamine groups have been attached. Eight classes of transesterification catalysts, including ion exchange resins with tertiary amine and quaternary ammonium groups, are disclosed in J F Knifton et al., J. Mol. Catal, 67 (1991) 389ff.

A suitable heterogeneous transesterification catalyst may be a catalyst comprising an element from Group 4 (such as titanium), Group 5 (such as vanadium), Group 6 (such as chromium or molybdenum) or Group 12 (such as zinc) of the Periodic Table of the Elements, or tin or lead, or a combination of such elements, such as a combination of zinc with chromium (for example zinc chromite). Said elements may be present in the catalyst as an oxide, such as zinc oxide. Preferably, in step (a) of the process of the present invention a heterogeneous catalyst comprising zinc is used.

The conditions in step (a) of the present process include a temperature of from 10 to 200° C., and a pressure of from 0.5 to 50 bara ($5 \times 10^4$ to $5 \times 10^6$ N/m$^2$). Preferably, especially in co-current operation, said pressure ranges from 1 to 20 bar, more preferably 1.5 to 20 bar, most preferably 2 to 15 bar, and said temperature ranges from 30 to 200° C., more preferably 40 to 170° C., most preferably 50 to 150° C.

Further, preferably an excess of the alkanol over the alkylene carbonate is used in step (a) of the present process. The molar ratio of alkanol to alkylene carbonate in the present process is suitably of from 1.01:1 to 25:1, preferably of from 2:1 to 20:1, more preferably of from 3:1 to 15:1, most preferably from 3:1 to 13:1.

Still further, the weight hourly space velocity (WHSV) in step (a) of the present process may suitably range of from 0.1 to 100 kg/kg$_{cat}$·hr ("kg$_{cat}$" refers to the catalyst amount), more suitably 0.5 to 50 kg/kg$_{cat}$·hr, more suitably 1 to 20 kg/kg$_{cat}$·hr, more suitably 1 to 10 kg/kg$_{cat}$·hr.

Step (a) of the present process may be carried out in a reactive distillation column, as described in U.S. Pat. No. 5,359,118. This would entail that the reaction is carried out counter-currently. The distillation column may contain trays with bubble caps, sieve trays, or Raschig rings. The skilled person will realise that several types of packings of catalyst and several tray configurations will be possible. Suitable columns have been described in, e.g., Ullmann's Encyclopedia of Industrial Chemistry, 5$^{th}$ ed. Vol. B4, pp 321 ff, 1992.

The alkylene carbonate will generally have a higher boiling point than the alkanol. In the case of ethylene and propylene carbonate the atmospheric boiling points are above 240° C. Therefore, in general, the alkylene carbonate will be fed at the upper part of a reactive distillation column and alkanol will be fed at the lower part of such column. The alkylene carbonate will flow downwardly, and the alkanol will flow upwardly.

Preferably, step (a) of the present process is conducted in a co-current manner. A suitable way to operate is to carry out the reaction in a trickle-flow manner wherein the reactants part in vapour phase and part in liquid phase drip down over the catalyst. A more preferred way to operate step (a) of the process of the present invention is in a reactor with only liquids. A suitable reaction zone of this type is a pipe-type reaction zone wherein the reaction is conducted in a plug flow manner. For example, step (a) of the present process may be carried out in one plug flow reactor or in a series of two or more plug flow reactors. This will enable the reaction to approach equilibrium.

A further possibility is to conduct step (a) of the process of the present invention in a continuously stirred tank reactor (CSTR). In the latter case the effluent from the CSTR is preferably subjected to a post-reaction in a plug flow reactor so that the reaction can approach equilibrium.

Step (a) of the process of the present invention is preferably carried out continuously. Further, unconverted alkylene carbonate and alkanol are preferably recycled.

Step (b) of the present process comprises separating unconverted alkylene carbonate and alkanediol from the product mixture obtained in step (a) to obtain a top stream containing unconverted alkanol, dialkyl carbonate and the ether alkanol impurity. Said step (b) may be effected by means of distillation. The bottom stream obtained in step (b) comprises unconverted alkylene carbonate and alkanediol.

Step (c) of the present process comprises recovering the alkanediol. Said step (c) may be effected by means of distillation. The alkanediol may be recovered by separating the bottom stream containing unconverted alkylene carbonate and alkanediol obtained in step (b) to obtain a top stream containing alkanediol and a bottom stream containing unconverted alkylene carbonate. Unconverted alkylene carbonate in said bottom stream may be recycled to step (a).

Step (d) of the present process comprises separating unconverted alkanol from the top stream obtained in step (b) to obtain a bottom stream containing dialkyl carbonate and the ether alkanol impurity. Said step (d) may be effected by means of distillation. The top stream obtained in step (d) comprises unconverted alkanol. Unconverted alkanol in said top stream may be recycled to step (a).

The separations and recovery of products in steps (b), (c) and (d) of the present process may be effected in any known way. For example, they may be recovered by applying the process as disclosed in WO2011039113, the disclosure of which is incorporated herein by reference.

The amount of the ether alkanol impurity in the bottom stream obtained in step (d) and containing dialkyl carbonate and said impurity may be comprised in the range of from 10 parts per million by weight (ppmw) to 10 wt. %, specifically 100 ppmw to 9 wt. %, more specifically 0.1 to 8 wt. %, more specifically 0.3 to 7 wt. %, more specifically 0.5 to 6 wt. % and most specifically 0.5 to 5 wt. %.

Step (e) of the present process comprises subjecting the bottom stream obtained in step (d), containing dialkyl carbonate and the ether alkanol impurity, to extractive distillation using an extraction solvent to obtain a top stream comprising dialkyl carbonate and a bottom stream comprising the ether alkanol impurity and the extraction solvent.

Further, step (f) of the present process comprises removing the ether alkanol impurity from the bottom stream obtained in step (e) and recycling the extraction solvent to step (e).

In step (e), the extraction solvent is preferably fed to the distillation column at a position which is above the position at which the stream containing dialkyl carbonate and the ether alkanol impurity is fed. The extraction solvent is preferably fed at the top of the column or a few trays below the top of the column. Most preferably, the extraction solvent is fed at the top of the column.

The column may be any suitable sort of column known in the art and may be equipped with trays or structured or unstructured packing. The number of theoretical trays may vary in the range of from 3 to 140 or 3 to 60 or 3 to 20.

Preferably, in step (e), the extraction solvent is added in an amount such that the weight ratio of the extraction solvent fed to the column to the stream containing dialkyl carbonate and the ether alkanol impurity fed to the column is at least 1:20, more preferably at least 1:10, most preferably at least 1:4. Further, preferably, the latter weight ratio is at most 10:1, more preferably at most 5:1, more preferably 2:1, most preferably at most 1.5:1.

The extractive distillation in step (e) may be carried out at a temperature in the range of from 50 to 250° C., preferably of from 100 to 200° C. and at a pressure of at least 0.1 kPa, preferably at least 10 kPa, more preferably at least 50 kPa. The pressure may be at most 400 kPa, preferably at most 200 kPa, more preferably at most 120 kPa.

In step (e), a top stream comprising dialkyl carbonate is removed from the distillation column preferably above the point at which the extraction solvent is fed to the distillation column. At least a portion of the dialkyl carbonate may advantageously be recovered as a high purity dialkyl carbonate product. The top stream comprising dialkyl carbonate obtained in step (e) may additionally comprise some unconverted alkanol which may be removed in an additional separation step.

Further, in step (e), a bottom stream comprising the ether alkanol impurity and the extraction solvent is removed from the distillation column. In step (f), the ether alkanol impurity is then removed from the latter bottom stream. This may be effected by separating the bottom stream comprising the ether alkanol impurity and the extraction solvent obtained in step (e) to obtain a top stream comprising the ether alkanol impurity and a bottom stream comprising the extraction solvent. Said separation may be effected by means of distillation in a distillation column or by separation in a flash vessel. Said separation is carried out at lower pressure or higher temperature than in extractive distillation step (e). At least a portion of the ether alkanol impurity may advantageously be recovered as a high purity ether alkanol product or as a mixture of ether alkanol and extraction solvent. The extraction solvent in said bottom stream is then recycled to step (e). A portion of the extraction solvent containing bottom stream obtained in step (e) may be removed as a bleed to prevent a build-up of any heavies. In case of such bleed, an extraction solvent containing make-up stream needs to be fed to step (e).

Further, the above-mentioned bottom stream comprising dialkyl carbonate and the extraction solvent obtained in step (e) may first be split wherein one split substream ("fat" extractant stream) is recycled to step (e) and another split substream is further separated, in above-mentioned step (f), into a top stream comprising the ether alkanol impurity and a bottom stream comprising the extraction solvent ("lean" extractant stream). Said "fat" extractant stream is preferably fed to the extractive distillation column in step (e) at a position which is below the position at which said "lean" extractant stream is fed to said column. Preferably, the weight ratio of said "fat" extractant stream to the other split substream is greater than 1:1, preferably greater than 3:1, more preferably greater than 5:1, most preferably greater than 7:1. An advantage of this is that a separation unit used in step (f) may be kept relatively small. Further, the latter weight ratio is preferably at most 50:1, more preferably at most 30:1, most preferably at most 20:1.

The present invention also relates to a process for removing an ether alkanol impurity from a stream containing a dialkyl carbonate and the ether alkanol impurity, comprising the above-described steps (e) and (f), that is to say:

(e) subjecting the stream containing a dialkyl carbonate and the ether alkanol impurity to extractive distillation using an extraction solvent to obtain a top stream comprising dialkyl carbonate and a bottom stream comprising the ether alkanol impurity and the extraction solvent, wherein the extraction solvent is an organic compound containing one or more ester moieties and/or ether moieties which organic compound does not contain a hydroxyl group; and (f) removing the ether alkanol impurity from the bottom stream obtained in step (e) and recycling the extraction solvent to step (e).

The above-described features, preferences and embodiments in relation to steps (e) and (f) as part of a process for the preparation of a dialkyl carbonate and an alkanediol, equally apply to the present process for removing an ether alkanol impurity from a stream containing a dialkyl carbonate and the ether alkanol impurity, which latter stream may originate from any other process, including processes other than processes for the preparation of a dialkyl carbonate and an alkanediol.

Further, in the present process for removing an ether alkanol impurity from a stream containing a dialkyl carbonate and the ether alkanol impurity, the dialkyl carbonate may be a di($C_1$-$C_4$ alkyl) carbonate, more suitably a di($C_1$-$C_3$ alkyl) carbonate, most suitably a di($C_2$-$C_3$ alkyl) carbonate. Further, preferably, said dialkyl carbonate is dimethyl carbonate, diethyl carbonate or diisopropyl carbonate, more preferably diethyl carbonate or diisopropyl carbonate, most preferably diethyl carbonate.

Still further, in the present process for removing an ether alkanol impurity from a stream containing a dialkyl carbonate and the ether alkanol impurity, the ether alkanol impurity is an alkoxy alkanol which is an alkanol of formula $R_3OH$ wherein $R_3$ is an alkoxyalkyl group. The alkoxy part in said alkoxyalkyl group is preferably methoxy, ethoxy or isopropoxy, more preferably ethoxy or isopropoxy, most preferably ethoxy. Further, the alkyl part in said alkoxyalkyl group is preferably ethyl or propyl, most preferably ethyl. The ether alkanol impurity may for example be 2-ethoxyethanol or 1-ethoxy-2-propanol and/or 2-ethoxy-1-propanol.

Further, as also mentioned in above in relation to the bottom stream obtained in step (d) of the present process for the preparation of a dialkyl carbonate and an alkanediol, in the present process for removing an ether alkanol impurity from a stream containing a dialkyl carbonate and the ether alkanol impurity, the amount of the ether alkanol impurity in the latter stream may be comprised in the range of from 10 parts per million by weight (ppmw) to 10 wt. %, specifically 100 ppmw to 9 wt. %, more specifically 0.1 to 8 wt. %, more specifically 0.3 to 7 wt. %, more specifically 0.5 to 6 wt. % and most specifically 0.5 to 5 wt. %.

Further, the present invention relates to a process for making a diaryl carbonate, comprising reacting an aryl alcohol with a stream containing a dialkyl carbonate from which stream an ether alkanol impurity has been removed in accordance with the above-described process.

Thus, the present invention relates to a process for making a diaryl carbonate, comprising contacting, in the presence of a transesterification catalyst, an aryl alcohol with a stream containing a dialkyl carbonate from which stream an ether alkanol impurity has been removed in accordance with any one of the above-described processes.

Further, the present invention also relates to a process for making a diaryl carbonate, comprising removing an ether alkanol impurity from a stream containing a dialkyl carbonate and the ether alkanol impurity in accordance with any one of the above-described processes, and then contacting, in the presence of a transesterification catalyst, an aryl alcohol with the stream containing the dialkyl carbonate.

Preferably, in the above-described processes for making a diaryl carbonate, the diaryl carbonate is diphenyl carbonate and the aryl alcohol is phenol.

In addition, the above-described transesterification catalyst and other transesterification conditions, as described for step (a), are equally applicable to said processes for making a diaryl carbonate.

The present process for the preparation of a dialkyl carbonate and an alkanediol is illustrated in FIG. 1. In FIG. 1, ethanol is passed via line 1 into a reactor 2. Reactor 2 can suitably be a continuously stirred tank reactor. Via line 3 ethylene carbonate is also fed into reactor 2. A transesterification catalyst may be present or may be fed continuously to the reactor. The catalyst may be mixed with one of the reactants or fed to the reactor via a separate line (not shown). A product mixture containing unconverted ethylene carbonate, unconverted ethanol, diethyl carbonate, ethylene glycol (an alkanediol) and 2-ethoxyethanol (an ether alkanol impurity; ethyl oxitol) is withdrawn from reactor 2 via line 4. Via line 4 the mixture is passed to a distillation column 5 where the product is separated into a top stream comprising diethyl carbonate, unconverted ethanol and ethyl oxitol that is withdrawn via line 7, and a bottom stream comprising ethylene glycol and unconverted ethylene carbonate that is withdrawn via line 6. The bottom stream in line 6 is subjected to distillation in a distillation column 8, resulting in a top stream comprising ethylene glycol that is recovered via line 10 and a bottom stream comprising unconverted ethylene carbonate that is recycled via lines 9 and 3 to reactor 2.

The top stream comprising diethyl carbonate, unconverted ethanol and ethyl oxitol originating from distillation column 5 is subjected to distillation in a distillation column 11, resulting in a top stream comprising unconverted ethanol that is recycled via lines 13 and 1 to reactor 2 and a bottom stream comprising diethyl carbonate, ethyl oxitol and unconverted ethanol. The latter bottom stream is fed via line 12 to the lower part of a distillation column 14. In said column, the stream comprising diethyl carbonate, ethyl oxitol and unconverted ethanol is subjected to extractive distillation using ethylene carbonate as the extraction solvent which is fed to the column at an upper part thereof. The resulting bottom stream in line 15 comprises ethyl oxitol and ethylene carbonate and is sent to separator 17 (which may be a distillation column or a flash vessel), resulting in a top stream comprising ethyl oxitol and optionally ethylene carbonate in line 19 and a bottom stream comprising ethylene carbonate in line 18. The latter bottom stream 18 is recycled to extractive distillation column 14 at an upper part thereof. Optionally, stream 15 may be split into two substreams 15a and 15b, wherein substream 15b is sent to separator 17 and substream 15a is recycled to extractive distillation column 14 at a position which is below the position at which stream 18 is fed to that column. The resulting top stream from distillation column 14 comprises diethyl carbonate and unconverted ethanol and is sent via line 16 to a distillation column 20, resulting in a top stream comprising unconverted ethanol that is recycled via lines 22 and 1 to reactor 2 and a bottom stream comprising diethyl carbonate in line 21.

The invention is further illustrated by the following Examples.

EXAMPLES

Isobaric Vapour-Liquid Equilibrium (VLE) data were measured by means of a dynamic method using a Swietoslawski ebulliometer as described by Rogalski and Malanowski, Fluid Phase Equilib. 5 (1980) 97-112. At a given pressure, which is regulated by an electronic pressure control, the boiling temperature of a mixture can be measured. When phase equilibrium is reached, i.e. a stable circulation is achieved and the boiling temperature is constant, the concentrations of both phases in equilibrium can be determined by taking samples from the liquid and the condensed vapour phase and gas chromatographic analysis. Such data correspond to the separation on one theoretical plate in a distillation column.

For the ternary system diethyl carbonate (DEC)+2-ethoxyethanol (oxitol)+ethylene carbonate isobaric VLE data were measured at 100.0 mbar with a fixed ethylene carbonate feed concentration (50 wt. %).

An ethylene carbonate-free data point was measured as reference at a boiling point of 61.39° C. and a pressure of 100.5 mbar, with a DEC mole fraction of 0.8193 and an oxitol mole fraction of 0.1807 in the liquid phase (x(DEC) and x(oxitol), respectively), and a DEC mole fraction of 0.8232 and an oxitol mole fraction of 0.1768 in the vapour phase (y(DEC) and y(oxitol), respectively). These data can be converted into distribution coefficients (K-values), where K(DEC) is equal to the vapour phase mole fraction of DEC divided by the liquid phase mole fraction of DEC. Similarly, the K-value of oxitol is calculated using the mole fractions of oxitol in the vapour and liquid phases. The relative volatility alpha (DEC/oxitol) can be defined as the ratio of the K-values of DEC and oxitol. At the azeotropic point, this relative volatility is 1 (one). The efficiency (selectivity and capacity) of a solvent to enhance the separation of oxitol from DEC can be assessed by monitoring the change of the relative volatility when adding such solvent.

Table 1 below shows VLE data as well as the derived K-values of DEC and oxitol and the relative volatility of DEC versus oxitol. An alpha value (relative volatility) higher than 1 means first of all that there is no azeotrope between DEC and oxitol, and secondly that the first component will move up and the second component will move down in a distillation column.

The data in Table 1 show firstly that by adding ethylene carbonate the relative volatility of DEC versus oxitol is higher than 1 in the full range of compositions evaluated, and that therefore the azeotrope between these two is advantageously broken, and secondly that DEC is the component that will move up in a distillation column and that oxitol will move down together with the ethylene carbonate. Thus, advantageously, ethylene carbonate is a good extraction solvent for separating oxitol from DEC in an extractive distillation process. Surprisingly, ethylene carbonate is a solvent that preferably dissolves oxitol and to a lesser extent DEC. In a further step, the oxitol may easily be separated from ethylene carbonate (e.g. by distillation) after which the ethylene carbonate can advantageously be re-used as extraction solvent in extractive distillation of oxitol and DEC mixtures.

TABLE 1

| T (° C.) | Liquid phase composition | | | Vapor phase composition | | | K (DEC) | K (oxitol) | alpha (DEC/oxitol) |
|---|---|---|---|---|---|---|---|---|---|
| | x(1) | x(2) | x(3) | y(1) | y(2) | y(3) | | | |
| No ethylene carbonate in feed | | | | | | | | | |
| 61.39 | 0.8193 | 0.1807 | 0 | 0.8232 | 0.1768 | 0 | 1.0048 | 0.9784 | 1.0269 |
| 50 wt. % ethylene carbonate in feed | | | | | | | | | |
| 79.46 | 0.0310 | 0.4452 | 0.5237 | 0.1248 | 0.8349 | 0.0403 | 4.024 | 1.875 | 2.146 |
| 78.64 | 0.0613 | 0.3917 | 0.5470 | 0.2421 | 0.7424 | 0.0155 | 3.948 | 1.896 | 2.082 |
| 77.37 | 0.0924 | 0.3468 | 0.5609 | 0.3395 | 0.6452 | 0.0153 | 3.676 | 1.861 | 1.975 |
| 75.68 | 0.1274 | 0.3093 | 0.5634 | 0.4237 | 0.5525 | 0.0238 | 3.326 | 1.787 | 1.861 |
| 74.55 | 0.1675 | 0.2781 | 0.5544 | 0.4990 | 0.4769 | 0.0241 | 2.979 | 1.715 | 1.737 |
| 73.32 | 0.1970 | 0.2258 | 0.5772 | 0.5687 | 0.4073 | 0.0240 | 2.886 | 1.804 | 1.600 |
| 72.64 | 0.2452 | 0.1915 | 0.5633 | 0.6394 | 0.3264 | 0.0342 | 2.607 | 1.704 | 1.530 |
| 71.36 | 0.2905 | 0.1420 | 0.5675 | 0.7270 | 0.2565 | 0.0165 | 2.502 | 1.807 | 1.385 |
| 71.82 | 0.3214 | 0.0952 | 0.5834 | 0.8074 | 0.1810 | 0.0117 | 2.512 | 1.901 | 1.321 |
| 71.24 | 0.3654 | 0.0485 | 0.5861 | 0.8920 | 0.0970 | 0.0110 | 2.441 | 2.001 | 1.220 | x(1) = x(DEC); x(2) = x(oxitol); x(3) = x(ethylene carbonate). Same applies to y(1), y(2) and y(3).

We claim:

1. Process for the preparation of a dialkyl carbonate and an alkanediol, comprising:
   (a) reacting an alkylene carbonate and an alkanol to obtain a product mixture containing unconverted alkylene carbonate, unconverted alkanol, dialkyl carbonate, alkanediol and an ether alkanol impurity;
   (b) separating unconverted alkylene carbonate and alkanediol from the product mixture to obtain a top stream containing unconverted alkanol, dialkyl carbonate and the ether alkanol impurity;
   (c) recovering the alkanediol;
   (d) separating unconverted alkanol from the top stream obtained in step (b) to obtain a bottom stream containing dialkyl carbonate and the ether alkanol impurity; and
   (e) subjecting the bottom stream obtained in step (d) to extractive distillation using an extraction solvent to obtain a top stream comprising dialkyl carbonate and a bottom stream comprising the ether alkanol impurity and the extraction solvent, wherein the extraction solvent is an organic compound containing one or more ester moieties and/or ether moieties which organic compound does not contain a hydroxyl group; and
   (f) removing the ether alkanol impurity from the bottom stream obtained in step (e) and recycling the extraction solvent to step (e).

2. Process according to claim 1, wherein the alkylene carbonate is a $C_2$-$C_6$ alkylene carbonate, and the alkanol is a $C_1$-$C_4$ alkanol.

3. Process according to claim 2, wherein the alkylene carbonate is ethylene carbonate or propylene carbonate, the alkanol is ethanol and the dialkyl carbonate is diethyl carbonate.

4. Process according to claim 1, wherein the extraction solvent is an ester of formula $R_1X(C=O)OR_2$ wherein X is absent or is an oxygen atom and wherein $R_1$ and $R_2$ comprise a total of 2 to 20 carbon atoms and do not contain a hydroxyl group.

5. Process according to claim 4, wherein the ester of formula $R_1X(C=O)OR_2$ is:
   an ester wherein X is absent which originates from reacting an alkanol of formula $R_2OH$ containing 1 or more hydroxyl groups with a carboxylic acid of formula $R_1(C=O)OH$, wherein all of the 1 or more hydroxyl groups of the alkanol are esterified; or
   an alkylene carbonate wherein X is an oxygen atom and $R_1$ and $R_2$ are connected to form a ring; or a carbonate wherein X is an oxygen atom and $R_1$ and $R_2$ are not connected to form a ring.

6. Process according to claim 5, wherein the alkylene carbonate used as extraction solvent in step (e) is identical to the alkylene carbonate used as reactant in step (a).

7. Process according to claim 1, wherein the extraction solvent is an ether of formula $R_4$—O—$R_5$ wherein $R_4$ and $R_5$ comprise a total of 2 to 20 carbon atoms and do not contain a hydroxyl group.

8. Process according to claim 7, wherein the ether of formula $R_4$—O—$R_5$ is:
   an ether of a polyalkylene glycol wherein the polyalkylene glycol contains two hydroxyl groups which are both etherified with an alkanol; or
   an ether of an alkanol of formula $R_4OH$ containing 1 or more hydroxyl groups and an alkanol of formula $R_5OH$ containing 1 or more hydroxyl groups, wherein all of the hydroxyl groups of said alkanols are etherified; or
   an acetal or a ketal.

9. Process for removing an ether alkanol impurity from a stream containing a dialkyl carbonate and the ether alkanol impurity, comprising:
   (e) subjecting the stream containing a dialkyl carbonate and the ether alkanol impurity to extractive distillation using an extraction solvent to obtain a top stream comprising dialkyl carbonate and a bottom stream comprising the ether alkanol impurity and the extraction solvent, wherein the extraction solvent is an organic compound containing one or more ester moieties and/or ether moieties which organic compound does not contain a hydroxyl group; and
   (f) removing the ether alkanol impurity from the bottom stream obtained in step (e) and recycling the extraction solvent to step (e).

10. Process for making a diaryl carbonate, comprising removing an ether alkanol impurity from a stream containing a dialkyl carbonate and the ether alkanol impurity in accordance with the process of claim 1, and then contacting, in the presence of a transesterification catalyst, an aryl alcohol with the stream containing the dialkyl carbonate.

11. The process according to claim 5, wherein the ester of formula $R_1X(C=O)OR_2$ is an alkylene carbonate wherein X is an oxygen atom and $R_1$ and $R_2$ are connected to form a ring, which alkylene carbonate is ethylene carbonate or propylene carbonate.

* * * * *